(12) United States Patent
Yang et al.

(10) Patent No.: US 10,564,140 B2
(45) Date of Patent: Feb. 18, 2020

(54) DIFFUSION CELL TESTING METHODS AND SYSTEM CONTAINING BIPHASIC RECEPTOR FLUIDS

(71) Applicant: BUFFERAD Illinois Inc., Lake Bluff, IL (US)

(72) Inventors: Wen Yang, Evanston, IL (US); Kenna Krone, Pleasant Prairie, WI (US); Jerry Z. Zhang, Long Grove, IL (US); Xiaoyan Xu, Long Grove, IL (US)

(73) Assignee: BUFFERAD Illinois Inc., Lake Bluff, IL (US)

( * ) Notice: Subject to any disclaimer, the term of this patent is extended or adjusted under 35 U.S.C. 154(b) by 382 days.

(21) Appl. No.: 15/483,316

(22) Filed: Apr. 10, 2017

(65) Prior Publication Data

US 2018/0292376 A1    Oct. 11, 2018

(51) Int. Cl.
*G01N 33/15*    (2006.01)
*G01N 13/00*    (2006.01)

(52) U.S. Cl.
CPC ............ *G01N 33/15* (2013.01); *G01N 13/00* (2013.01); *G01N 2013/003* (2013.01); *G01N 2013/006* (2013.01)

(58) Field of Classification Search
CPC .. G01N 33/15; G01N 13/00; G01N 2013/006; G01N 2013/003
See application file for complete search history.

(56) References Cited

U.S. PATENT DOCUMENTS

| | | | | |
|---|---|---|---|---|
| 5,998,365 | A * | 12/1999 | Sherman | A61K 9/1075 424/455 |
| 10,137,106 | B2 * | 11/2018 | Alkon | A61K 31/519 |
| 2007/0066761 | A1 * | 3/2007 | Deetz | C08F 2/42 525/309 |
| 2012/0302502 | A1 * | 11/2012 | Botti | A61K 9/006 514/11.7 |
| 2016/0102236 | A1 * | 4/2016 | Alwattari | C04B 28/02 166/278 |

OTHER PUBLICATIONS

Proniuk, Stefan et al. "Investigation of the Utility of an In Vitro Release Test for Optimizing Semisolid Dosage Forms" Pharmaceutical Development and Technology, 6(3), 469-476 (2001). (Year: 2001).*

* cited by examiner

*Primary Examiner* — Paul M. West
(74) *Attorney, Agent, or Firm* — Beem Patent Law Firm

(57) ABSTRACT

An in vitro release testing method and system for testing the ability of formulations to deliver agents across a barrier membrane is disclosed. The method may comprise steps of providing a dosage of a semi-solid formulation containing the bioactive agent, a receptor solution, and a barrier membrane to separate the semi-solid formulation and the receptor solution. The receptor solution may be a biphasic solution or an immiscible solution. The semi-solid formulation may be contacted with one side of the barrier membrane and the receptor solution with the other side of the barrier membrane for a time sufficient to produce penetration of the barrier membrane by the semi-solid formulation. The receptor solution may be sampled and assayed to determine the concentration of the bioactive agent in the receptor solution.

39 Claims, 1 Drawing Sheet ic fluid is
commonly a homogenous solvent system. It might be a
single solvent or suitable mixture of miscible solvents.
DIFFUSION CELL TESTING METHODS AND SYSTEM CONTAINING BIPHASIC RECEPTOR FLUIDS

BACKGROUND OF THE INVENTION

In general, the present disclosure relates to methods and systems for studying the release and diffusion behavior of semi-solid dosage products. In particular, this disclosure relates to the use of a barrier membrane in the study of penetration of bioactive agents in diffusion cell testing using biphasic solvent systems as receptor fluids.

Diffusion cell testing is a common method to study diffusion of a pharmaceutically active compound through tissue. The tissue comprises human or animal tissues, such as, e.g., skin, ocular, buccal, lung, or synthetic membranes. A common method to perform diffusion cell testing is by mounting a piece of tissue between two chambers (donor and receptor chamber). The donor chamber is typically dosed with a pharmaceutically active compound or drug. The receptor chamber is filled with solvent systems, referred to as receptor fluids, to solubilize the compound released from the donor chamber and diffused through the tissue. The receptor fluids are in intimate contact with the mounted tissue in order to solubilize the compound released from the donor chamber and diffused through the tissue.

When a synthetic membrane is used in the diffusion cell testing, the testing is commonly referred to as in vitro release testing (IVRT). IVRT is a common method to study release of a pharmaceutically active compound from semi-solid dosage forms (including ointments, creams, lotions, pastes, and other viscous liquids). In an IVRT, the receptor fluid has two functions: one is as a medium to drive release of the pharmaceutically active compound from the semi-solid dosage forms. The other is as a medium to solubilize the released compound to drive continuation of the release process.

Selection of a suitable receptor fluid is one of most important factors in successfully carrying out an IVRT. To select a suitable receptor fluid, solubility of the pharmaceutically active compound in the fluid needs to be tested to determine if the receptor fluid has adequate solubility for the compound. Solubility of a compound may be determined in a homogenous solvent system. Therefore, receptor fluid is commonly a homogenous solvent system. It might be a single solvent or suitable mixture of miscible solvents.

Depending on exact nature of semi-solid dosage forms, they generally have various degrees of viscosity. The selected receptor fluid needs to drive release of the pharmaceutically active compound from the viscous dosage forms. When a semi-solid dosage form contains a pharmaceutically active compound that has very different physical and chemical property from the dosage form base, selection of a suitable receptor fluid becomes extremely challenging. For example, it is very difficult to select a suitable receptor fluid for an ointment dosage form containing a hydrophilic pharmaceutically active compound in a petrolatum base. Due to highly lipophilic nature of petrolatum base, the receptor fluid must possess high lipophilic property to reduce viscosity of the petrolatum base and drive release of the hydrophilic compound from the petrolatum base. The released hydrophilic compound must, in turn, be efficiently solubilized in the receptor fluid to keep the release process continuing. However, a hydrophilic compound generally has low solubility in a receptor fluid with high lipophilic property. Finding a suitable receptor fluid with favorable ratio of hydrophilicity and lipophilicity is a very tedious process. It requires selecting a large number of solvent systems and conducting a large numbers of IVRT experiments to determine if a selected receptor fluid is suitable. Thus, improvements in conducting IVRT are needed.

BRIEF SUMMARY OF THE INVENTION

The present disclosure relates, in various embodiments, to a system. The system can comprise one or more diffusion cells. The one or more diffusion cells can comprise a donor compartment, a barrier membrane, and a receptor compartment. The receptor compartment can have a biphasic solution.

The present disclosure relates, in various embodiments, to at least an in vitro release method for testing the ability of formulations to deliver bioactive agents across a barrier membrane. The method may comprise the steps of providing a dosage of a semi-solid formulation containing the bioactive agent, a receptor solution and a barrier membrane to separate the semi-solid formulation and the receptor solution. The receptor solution may be a biphasic solution or an immiscible solution. The semi-solid formulation may be contacted with one side of the barrier membrane and the receptor solution with the other side of the barrier membrane for a time sufficient to produce penetration of the barrier membrane by the semi-solid formulation. The receptor solution may be sampled and assayed to determine the concentration of the bioactive agent in the receptor solution.

The present disclosure relates, in various embodiments, to a receptor solution in a system for testing a membrane behavior of a bioactive agent comprising a barrier membrane positioned between a donor formulation and a receptor solution. The receptor solution can comprise an immiscible solution.

The present disclosure relates, in various embodiments, to a system. The system for testing a bioactive agent comprising a donor formulation and a receptor solution. The receptor solution may comprise a biphasic solution. The biphasic solution may comprise one hydrophilic solution and at least one hydrophobic solution.

DETAILED DESCRIPTION OF THE INVENTION

Figure 1:
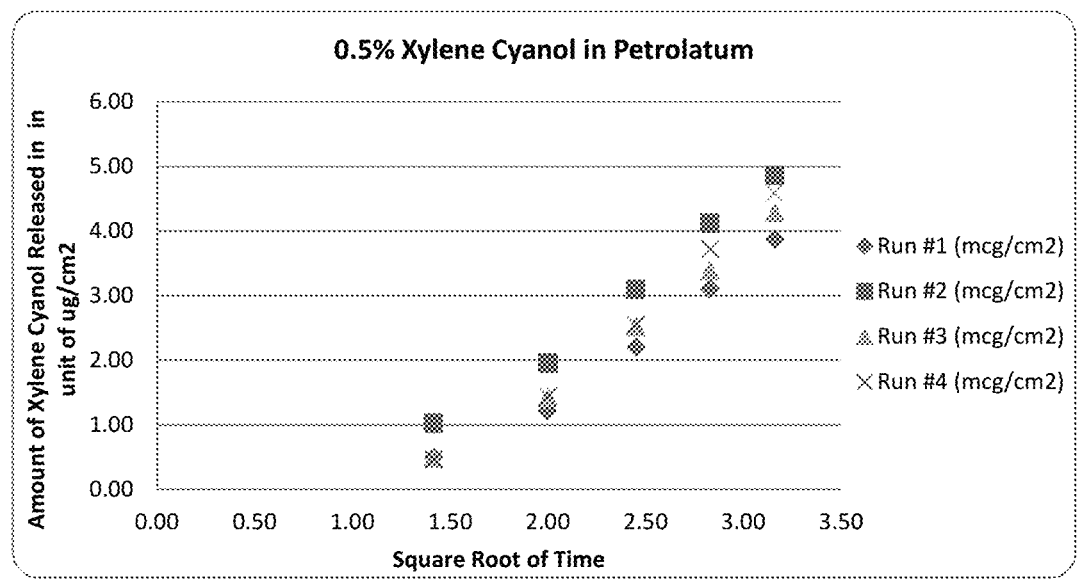
FIG. 1 illustrates an amount of xylene cyanol released in microgram per square centimeters of the membrane as a function of square root of release time in hours according to one embodiment.

The present disclosure can be understood more readily by reference to the following detailed description, drawings, examples, and claims, and their previous and following description. However, before the present compositions, articles, devices, and methods are disclosed and described, it is to be understood that this disclosure is not limited to the specific compositions, articles, devices, and methods disclosed unless otherwise specified, as such can, of course, vary. It is also to be understood that the terminology used herein is for the purpose of describing particular aspects only and is not intended to be limiting.

The following description of the disclosure is provided as an enabling teaching of the disclosure in its currently known embodiments. To this end, those skilled in the relevant art will recognize and appreciate that many changes can be made to the various aspects of the disclosure described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

Reference will now be made in detail to the present preferred embodiment(s), examples of which are illustrated in the accompanying drawings. The use of a particular reference character in the respective views indicates the same or like parts.

As noted above, broadly, this disclosure teaches a system for testing a membrane behavior of a bioactive agent comprising a barrier membrane positioned between a donor formulation and a receptor solution. The receptor solution can comprise an immiscible solution or a biphasic solution. The immiscible solution can comprise at least one hydrophilic solution and at least one hydrophobic solution. The at least one hydrophilic solution and at least one hydrophobic solution can help break down a semi solid formulation so that the semi solid formulation can penetrate through the membrane and diffuse into the receptor solution.

In conducting in vitro release testing, in addition to selection of a suitable synthetic membrane, a suitable receptor fluid must be selected. The solution can be a single solvent or a homogenous mixture of miscible solvents. Therefore, a receptor fluid is often referred to as a receptor solution.

A common method for selection of a receptor fluid is to select a solvent or homogenous mixture of miscible solvents and determine saturation solubility concentration of the pharmaceutically active compound in the selected solvent system. In general, the saturation solubility concentration should be at least an order of magnitude higher than highest sample concentration of the compound obtained in an in vitro release testing. By definition, solubility of a compound in a solvent or solvent mixture is amount of the compound solubilized in a homogenous solvent or mixture at saturation.

After initial selection of the receptor fluid, a pilot in vitro release testing is conducted. If the saturation solubility is not at least an order of magnitude higher than the highest sample concentration in the receptor fluid, the receptor fluid needs to be re-selected. Then, another in vitro release testing is conducted again. The process will be repeated until the saturation solubility is at least an order of magnitude higher than the highest sample concentration in the receptor fluid. The released compound must be properly solubilized in the selected receptor fluid. For example, in guidance for industry by U.S. Food and Drug Administration (FDA), such a solubility requirement in an in vitro release testing (IVRT) is clearly described, such as, in U.S. FDA "Draft Guidance on Acyclovir" Recommended December 2014; Revised December 2016.

The selected receptor fluid might have suitable solubilization ability to solubilize the released pharmaceutically active compound. Proper solubilization of the released compound can be achieved only after the compound can be released from the semi-solid dosage forms. The selected receptor fluid needs to cause release of the compound from the semi-solid dosage forms. Thus, a suitable receptor fluid needs to meet the release and solubilization requirements.

In a semi-solid dosage form, if a pharmaceutically active compound has very different physical and chemical properties from the dosage form base, selection of a suitable receptor fluid is a very tedious and extremely challenging process. Furthermore, after selection of the receptor fluid from the solubility test, it needs to be evaluated in an in vitro release testing experiment to confirm its suitability to obtain required testing results. The required results consist of requirements such as, linear and proportional release of the compound, for example. Generally speaking, if the receptor fluid does not drive release of the compound from the viscous dosage form, or the released pharmaceutically active compound does not have an adequate solubility in the selected receptor fluid, the testing results are generally unsatisfactory. If the results are unsatisfactory, cycle of receptor fluid selection and IVRT experiments of the selected receptor fluid are to be repeated again and again until satisfactory results are obtained.

Additionally, if there are two or more pharmaceutically active compounds in a semi-solid dosage form, selection of a suitable receptor fluid is even more challenging, particularly when the two or more compounds have different physical and chemical properties.

It has been unexpectedly discovered that conducting in vitro release testing is able to be improved by using a biphasic receptor fluid comprising at least two immiscible solvents.

The two immiscible solvents might be any solvents that are not miscible with each other. For example, both of the two immiscible solvents might be organic solvents or one aqueous-based solvent and one organic solvent. It is preferred that the receptor fluid comprises one aqueous-based solvent and one organic solvent that is immiscible with said aqueous-based solvent.

A "biphasic solution," as used herein, is a solution is added to another solution, such as an aqueous solution, so that the two phases reside in separated layers and form an interface.

An immiscible solvent is generally defined as a solvent having less than about 10% solubility in another solvent. For example, a water-immiscible organic solvent is generally defined as a solvent having less than about 10% solubility in water.

As used herein, the term 'about' will be understood by persons of ordinary skill in the art and will vary to some extent on the context in which is used. If there are uses of the term which are not clear to persons of ordinary skill in the art given the context in which is used, 'about' will mean up to plus or minus 10% of the particular term.

In one aspect, the present disclosure is directed to a method to conduct in vitro release testing by using the biphasic solvent system as the receptor fluid. In particular, the method may comprise steps of providing a dosage of a semi-solid formulation containing the bioactive agent, a receptor solution, and a barrier membrane to separate the semi-solid formulation and the receptor solution. The receptor solution may be a biphasic solution or an immiscible solution. The semi-solid formulation may be contacted with one side of the barrier membrane and the receptor solution with the other side of the barrier membrane for a time sufficient to produce penetration of the barrier membrane by the semi-solid formulation. The receptor solution may be sampled and assayed to determine the concentration of the bioactive agent in the receptor solution. In another aspect, the method may comprise steps of providing a dosage of a semi-solid formulation containing the bioactive agent and a receptor solution without a barrier membrane. The semi-solid formulation can be deposited in a donor compartment. The receptor solution may be in contact with the semi-solid formulation in the donor compartment. In yet another aspect, the semi-solid formulation can be put in a pouch in a donor compartment. In still another aspect, the semi-solid formulation can be floated in a donor compartment and can be in contact with the receptor fluid.

In another aspect, the present disclosure is directed to a system for conducting in vitro release testing by using the biphasic solvent system as the receptor fluid. The system comprises one or more diffusion cells that include a donor compartment, a barrier membrane, and a receptor compartment. The receptor compartment has a biphasic solution. The biphasic solution is in contact with the barrier membrane. The biphasic solution may have two or more immiscible solutions.

In a further aspect, the present disclosure is directed to a system for testing a bioactive agent comprising a barrier membrane positioned between a donor formulation and a receptor solution. The receptor solution may comprise an immiscible solution. In another aspect, the present disclosure is directed to a system for testing a bioactive agent comprising a donor formulation and a receptor solution without a barrier member. The bioactive agent can be deposited in a donor compartment without a barrier member as a support.

The biphasic solvent system consists of preferably a lipophilic phase and a hydrophilic, such as an aqueous-base phase which is immiscible with the lipophilic phase. It is believed that release of a pharmaceutically active compound from a semi-solid dosage form is driven by its diffusion through the dosage form and solubilization in the receptor fluid. Diffusion of a compound in a medium or dosage form depends on factors such as, viscosity of the medium or dosage form. Higher viscosity may mean slower diffusion. For example, a pharmaceutically active compound in a solid dosage form, such as, e.g., a solid tablet, will not diffuse out of the solid tablet unless the solid tablet is eroded or dissolved in presence of a solvent. In other words, solid matrix in the tablet has such a high viscosity that the active compound is not going to be released unless a solvent is coming in intimate contact with the tablet to cause erosion or dissolution of the solid matrix. Semi-solid dosage forms typically have various degrees of viscosities. For example, petrolatum-based ointments generally have relatively high viscosity, whereas lotions generally have relatively low viscosity.

Semi-solid dosage forms are dosage forms either comprised of immiscible phases, such as, a cream or lotion, which comprises an aqueous and oil phase, or a viscous matrix, such as, paste or ointment, with a pharmaceutically active compound dispersed or dissolved in the matrix. Function of a receptor fluid is thought to lower the viscosity of a semi-solid dosage form through erosion or dissolution, thereby causing release of a pharmaceutically active compound and subsequent solubilization of the released compound. When the dosage form and pharmaceutically active compound have different lipophilic/hydrophilic properties, a receptor fluid needs to have a balanced lipophilicity and hydrophilicity for release and solubilization of the compound.

A lipophilic compound may be more likely to be solubilized in a lipophilic solvent. A hydrophilic compound may be more likely to be solubilized in an aqueous-based solvent. In a homogeneous-phase receptor fluid, it commonly comprises a mixture of a water-miscible lipophilic solvent and an aqueous-based solvent to achieve the balanced lipophilicity and hydrophilicity.

If the pharmaceutically active compound in a semi-solid dosage form is lipophilic, presence of an aqueous-based solvent in the homogeneous-phase receptor fluid leads to decrease in its solubilization. On the other hand, if the pharmaceutically active compound in a semi-solid dosage form is hydrophilic, presence of a lipophilic solvent in the homogeneous-phase receptor fluid may also lead to decrease in its solubilization. Moreover, a semi-solid dosage form might contain two or more pharmaceutically active compounds which might have different properties. It is a rather tedious process to select a homogeneous-phase receptor fluid with a suitable balance of lipophilicity-hydrophilicity.

A biphasic receptor fluid of the present disclosure eliminates the need of the tedious and challenging cycle of selecting and testing the receptor fluid. Moreover, a biphasic receptor fluid teaches a method of conducting in vitro release testing. When an in vitro release test is conducted in a biphasic receptor fluid, the two immiscible phases act independently and yet collectively to drive release and solubilization of the pharmaceutically active compound. Furthermore, unlike in a one-phase homogeneous receptor fluid, presence of one solvent phase in the biphasic receptor fluid does not impede function of the other solvent.

A one-phase homogeneous receptor fluid may possess a balanced lipophilicity and hydrophilicity in order to drive release and solubilization of the compound. That requires a mixture of lipophilic and aqueous-based solvents. Presence of an aqueous-based solvent lowers overall lipophilicity of the one-phase receptor fluid, making it difficult, or even worse, impossible to drive release of the compound from the semi-solid dosage form. In order to improve or achieve the compound release, increase in overall lipophilicity of the receptor fluid is needed. Thus, ratio of the aqueous-based solvent in the fluid needs to become lower and lower. But, the released compound becomes less soluble in the receptor fluid with a lowered ratio of the aqueous-based solvent. Unsatisfactory IVRT may result in either case.

In the biphasic receptor fluid, lipophilic and hydrophilic solution, such as aqueous-based solvents, may act independently. Lipophilic solvent may help release of the pharmaceutically active compound. Since the aqueous-based solvent is not miscible with the lipophilic solvent, there is no decease in lipophilicity in the lipophilic solvent. Through proper selection, it possesses necessary lipophilicity to drive release of the compound. The released compound is then solubilized in the aqueous-based solvent. Since the lipophilic solvent is not miscible with the aqueous-based solvent, it possesses necessary solubilization power for the given selection. Functions of driving release and solubilization of the compound are handled independently by each individual phase of the biphasic receptor fluid. Collectively, a satisfactory IVRT experiment is conducted.

After a pharmaceutically active compound is released from a semi-solid dosage form into the biphasic receptor fluid, the released compound is solubilized in either one or both of the phases depending on relative solubility of the compound in each of the phases. For example, a highly lipophilic compound is mostly solubilized in the lipophilic phase. A highly hydrophilic compound is mostly solubilized in the aqueous-based phase. Other compounds are solubilized in both of the phases in a ratio according to their respective solubility in each phase. Since the two phases are immiscible with each other, solubilization of the compound in each individual phase might be independently optimized without presence of a solvent which has an opposite effect on the solubilization. The biphasic receptor fluid may eliminate tedious process of screening a large number of solvent combinations in order to find a suitable receptor fluid with the necessary lipophilicity-hydrophilicity balance. Thus, it is believed that the biphasic receptor fluid of the present disclosure is advantageous over the homogenous-phase receptor fluid.

Pharmaceutically active compounds have diverse solubility profiles in various organic solvents. In a homogeneous-phase receptor fluid, miscibility requirement of a lipophilic solvent with an aqueous-based solvent limits choice of lipophilic or aqueous-based solvent that can be selected. Moreover, in the aqueous-based solvent, other ingredients might be added to provide certain functionality, such as, e.g., pH-buffering agents. Presence of the other ingredients might further reduce miscibility of the aqueous-based solvent with the lipophilic solvent in a homogeneous-phase receptor fluid, thereby making the selection even more tedious. In the biphasic receptor fluid of the present disclosure, there is no miscibility requirement. Selection and optimization of the lipophilic and aqueous-based solvent are further improved.

A solvent that is immiscible with another solvent may be suitable according to the present disclosure. The solvent might be an organic-based or aqueous-based. Specifically, any organic solvent which is immiscible with an aqueous-based solvent may be suitable according to the present disclosure.

In one embodiment, a receptor fluid comprising of three or more immiscible solvents is also within scope of the present disclosure.

In some embodiments, the at least one hydrophobic solution may be a suitable organic solvent. In some embodiments, the at least one hydrophobic solution is an alcohol with five or more carbons, such as an alkyl alcohol, esters, alkanes, alkenes, and combinations thereof.

In some embodiments, a suitable alkyl alcohol may include monohydric alcohols or polyhydric alcohols.

In some embodiments, a suitable monohydric alcohol may be selected from a group consisting of primary, secondary, or tertiary alcohol. In some embodiments, suitable primary monohydric alcohols may be selected from a group consisting 1-pentanol, 1-hexanol, 1-heptanol, 1-octanol, 1-nonanol, 1-decanol, 1-undecanol, and combinations thereof. For primary monohydric alcohols that are solid at room temperature, their mixtures with primary monohydric alcohols that are liquid at room temperature are also suitable.

In some embodiments, a suitable secondary monohydric alcohol may be selected from a group consisting of cyclopentanol, cyclohexanol, 3-pentanol, 2-hexanol, 3-hexanol, 2-heptanol, 2-octanol, a derivative or combinations thereof.

In some embodiments, suitable polyhydric alcohols may be selected from 1,2-heptanediol, 1,2-octanediol, and combinations thereof.

In some embodiments, suitable esters may be selected from ethyl acetate, caprylic/capric triglyceride, isopropyl myristate, isopropyl palmitate, diisopropyl adipate, and combinations thereof. Oils generally are esters of glycerin and various fatty acids and may be suitable as hydrophobic or lipophilic solvents. In some embodiments, suitable oils may be selected from castor oil, olive oil, coconut oil, cochin oil, corn oil, cottonseed oil, linseed oil, palm oil, palm kernel oil, peanut oil, soybean oil, sunflower oil, tall oils, tallow, tung oil, whale oil, tea seed oil, sesame seed oil, safflower oil, rapeseed oil, fish oils, a derivative thereof, or a combination thereof.

In some embodiments, examples of suitable alkanes may be selected from a group consisting of isododecane, squalane, or a derivative thereof, or combinations thereof.

In some embodiments, an aqueous-based solvent which is immiscible with the organic solvent of the present disclosure may be suitable according to the present disclosure.

In further embodiment, a suitable aqueous-based solvent include water and water solutions. In some embodiments, the water solutions may be selected from a group consisting salts, pH-adjusting agents, anti-oxidants, buffering agents, preservatives, and combinations thereof. In some embodiments, the water solutions might also contain water-miscible organic solvents. In some embodiments, the water-miscible organic solvents do not make the aqueous-based solvent miscible with the lipophilic phase of the present disclosure.

In some embodiments, water-miscible solvents may be selected from a group consisting of monohydric alcohols, polyhydric alcohols, polyalkenyl alcohols, N-alkyl-2-pyrrolidones, isosorbide type of solvents, dimethyl sulfoxide, dimethylformide, dimethyl acetamide, and combinations thereof.

In some embodiments, monohydric alcohols are selected from a group consisting of ethanol, 1-propanol, isopropanol, and 1-butanol. In some embodiments, polyhydric alcohols are selected from a group consisting of glycerin, propylene glycol, butylene glycol, and hexylene glycol. Examples of polyalkenyl alcohols are low molecular weight polyethylene glycols (PEGs), such as e.g., PEG 200, PEG 300, PEG 400, and PEG 600. In some embodiments, N-alkyl-2-pyrrolidones are selected from a group consisting of N-methyl-2-pyrrolidone, N-ethyl-2-pyrrolidone, and N-propyl-2-pyrrolidone. In further embodiments, isosorbide type of solvents is selected from a group consisting of dimethyl isosorbide and diethyl isosorbide.

Selection of the two solvent phases may depend on solubility of the pharmaceutically active compound in each individual phase. The compound may need to have sufficient solubility in at least one of the two immiscible phases. If two or more pharmaceutically active compounds are present in a semi-solid dosage form, each of the compounds needs to be evaluated individually in the two immiscible phases. Moreover, at least one of the solvents needs to satisfactorily drive release of the compound from the dosage form.

Volume ratio of the two immiscible phases in the biphasic receptor fluid of the present disclosure might be in the range from 99 to 1 to 1 to 99, preferably from 70 to 30 to 30 to 70, more preferably from 60 to 40 to 40 to 60, for example.

Lipophilic phase and aqueous-based phase of the present disclosure might be prepared separately. The prepared phases might then be combined to yield the biphasic receptor fluid. Alternatively, all solvents and other ingredients, if required, might be combined together through mixing to yield the biphasic receptor fluid of the present disclosure. Each individual phase of the present disclosure is a homogeneous solution. Combination of the phases is a biphasic system. The biphasic receptor fluid has two phases. When the receptor fluid is placed in a static diffusion cell, one phase would be at top and the other one at bottom depending on their relative density. Generally speaking, hydrophilic solvents, such as water, may have higher density than a typical organic solvent. Thus, the aqueous-based phase is generally the bottom phase and the lipophilic phase is generally the top phase, for example. However, the density of each phase might be adjusted so that the aqueous-based phase might be on the top. For example, adding a water-miscible solvent of low density, such as, e.g., ethanol, to the aqueous-based phase might lower its density so that the lipophilic phase might reside on the top.

Typically, the phase at the top in the receptor chamber that is in intimate contact with the membrane is preferred to be the phase that has similar lipophilicity/hydrophilicity with the semi-solid dosage form being tested. For example, for an ointment form, the lipophilic phase is preferred to be the top phase.

After the biphasic receptor fluid is prepared, it might be used in an in vitro release testing experiment. It is known in the art that in vitro release testing might be performed in a static or flow-through diffusion cell setup. In the static setup, the receptor fluid is placed directly into the receptor compartment of a diffusion cell. In the flow-through setup, the receptor fluid is circulating into and through the receptor compartment using a pumping mechanism. The biphasic receptor fluid might be placed in a solvent reservoir which might then be circulated into and through the receptor compartment. For conducting in vitro release testing using a biphasic receptor fluid of the present disclosure, the static setup is preferred.

During an IVRT experiment, the two immiscible phases might be mixed with a suitable mixing mechanism. The mixed two immiscible phases may remain a heterogeneous two-phase system. In addition, during the experiment, due to heterogeneous nature of the two immiscible phases and selected mixing mechanism, one or both of the immiscible phases might be in intimate contact with the membrane in the diffusion cell setup.

Samples might be pulled out for analysis at a pre-determined time interval. Collection of the samples might be accomplished either by removing entire content of the receptor fluid and replacing it with a fresh batch or by pulling out a certain volume from each of the phases and replacing each phase with the same volume of the solvent. The entire replacement method may be preferred for the biphasic receptor fluid. The collected samples from each phase might be analyzed individually. Total amount of the compound release might then be calculated from the individual analysis.

The following examples are included for purposes of illustrating the technology covered by this disclosure. They are not intended to limit the scope of the claimed disclosure in any manner. One skilled in the art will understand that there are alternatives to these specific embodiments that are not completely described by these examples.

EXAMPLE 1

In Vitro Release Testing Method.

Release of pharmaceutically active compounds from semi-solid dosage forms was evaluated in an in vitro model of static vertical diffusion cell using a synthetic membrane model. In vitro release testing (IVRT) of the active compound into a biphasic receptor fluid was measured over a time period of 10 hours. The samples were analyzed using a UV-VIS spectrometer.

Xylene Cyanol was selected as the model pharmaceutically active compound for the IVRT experiments according to the present disclosure.

IVRT Experimental Conditions:

Test temperature: 32° C.

Test time points: 0, 2, 4, 6, 8, and 10 hours. Each test was conducted in four replicates (N=4). Square root of test time points: 0, 1.41, 2.00, 2.45, 2.83, and 3.16.

Membrane: Polypropylene (pore size: 0.45 micron).

Static vertical diffusion cell parameters: Area of the membrane diffusion area: 0.95 square centimeters.

Dosing level: infinite dose at about 3.0 milliliter of the semi-solid dosage form.

Static vertical diffusion cell consists of a donor and receptor compartment separated by a synthetic membrane. The dosing compartment was for the dosed semi-solid dosage form. The receptor compartment was filled with a biphasic receptor fluid. Before dosing, the diffusion cell was pre-incubated at 32° C. for about 20 to 45 minutes. The t=0 samples were taken after the incubation period prior to dosing.

During the experiment, the receptor fluid was in intimate contact with the membrane through a mixing mechanism, such as, e.g., magnetic stirring bar, or orbit shaker, and maintained at 32° C. using a heating mechanism, such as, e.g., dry heat block, or circulating water bath. At each time point, entire content of the receptor fluid was collected and replaced with a fresh batch pre-incubated at 32° C.

EXAMPLE 2

Preparation of a Semi-Solid Dosage Form

An ointment dosage form was prepared as an example of the semi-solid dosage form. Petrolatum was heated to about 50 to 70° C. while mixing. Xylene Cyanol was added to the heated petrolatum while heating and mixing. The mixture was mixed until uniform. Then, the mixture was slowly cooled to room temperature while mixing to yield the ointment formulation.

Ointment Dosage Form

| Ingredients | Percentage (%) |
| --- | --- |
| Xylene cyanol | 0.5 |
| Petrolatum | 99.5 |

EXAMPLE 3

In Vitro Release Testing (Comparative).

The ointment containing Xylene Cyanol was used in the in vitro release testing. The receptor fluid was water (one-phase solvent system). Total volume of the receptor fluid is 12.0 milliliter.

The following tables contain a summary of the results.

| Sample Collection Point | Run #1 (mcg/cm2) | Run #2 (mcg/cm2) | Run #3 (mcg/cm2) | Run #4 (mcg/cm2) |
| --- | --- | --- | --- | --- |
| API 0.5% Xylene Cyanol in Petrolatum Square root of time (hr) | Xylene Cyanol Infinite Dose, Receptor Fluid: water | | | |
| 0.00 | BDL | BDL | BDL | BDL |
| 1.41 | BDL | BDL | BDL | BDL |
| 2.00 | BDL | BDL | BDL | BDL |
| 2.45 | BDL | BDL | BDL | BDL |
| 2.83 | BDL | BDL | BDL | BDL |
| 3.16 | BDL | BDL | BDL | BDL |

-continued

|  | Run #1 (mcg/cm2) | Run #2 (mcg/cm2) | Run #3 (mcg/cm2) | Run #4 (mcg/cm2) |
|---|---|---|---|---|
| Slope | BDL | BDL | BDL | BDL |
| Slope - Average | Not applicable | Not applicable | Not applicable | Not applicable |
| Slope - Standard deviation | Not applicable |  |  |  |
| Coefficient of variation | Not applicable |  |  |  |
| R Squared | Not applicable | Not applicable | Not applicable | Not applicable |

BDL: Below detection limit.

The results showed that there was no release of Xylene Cyanol into the one-phase receptor fluid. Thus, water as a receptor fluid did not yield satisfactory results.

EXAMPLE 4

In Vitro Release Testing (Comparative).

The ointment containing Xylene Cyanol was used in the in vitro release testing. The receptor fluid was isopropyl alcohol (one-phase solvent system). Total volume of the receptor fluid is 12.0 milliliter.

The following tables contain a summary of the results.

|  | Run #1 (mcg/cm2) | Run #2 (mcg/cm2) | Run #3 (mcg/cm2) | Run #4 (mcg/cm2) |
|---|---|---|---|---|
| Sample Collection Point |  |  |  |  |
| API 0.5% Xylene Cyanol in Petrolatum Square root of time (hr) | Xylene Cyanol Infinite Dose, Receptor Fluid: isopropyl alcohol | | | |
| 0.00 | BDL | BDL | BDL | BDL |
| 1.41 | BDL | BDL | BDL | BDL |
| 2.00 | BDL | BDL | BDL | BDL |
| 2.45 | BDL | BDL | BDL | BDL |
| 2.83 | BDL | BDL | BDL | BDL |
| 3.16 | BDL | BDL | BDL | BDL |
| Slope | Not applicable | Not applicable | Not applicable | Not applicable |
| Slope - Average | Not applicable |  |  |  |
| Slope - Standard deviation | Not applicable |  |  |  |
| Coefficient of variation | Not applicable |  |  |  |
| R Squared | Not applicable | Not applicable | Not applicable | Not applicable |

BDL: Below detection limit.

The results showed that there was no release of Xylene Cyanol into the one-phase receptor fluid. Thus, isopropyl alcohol as a receptor fluid did not yield satisfactory results.

EXAMPLE 5

In Vitro Release Testing (Comparative).

The ointment containing Xylene Cyanol was used in the in vitro release testing. The receptor fluid was isopropyl alcohol:water in a ratio of 50 to 50 in volume (one-phase solvent system). Total volume of the receptor fluid is 12.0 milliliter.

The following tables contain a summary of the results.

|  | Run #1 (mcg/cm2) | Run #2 (mcg/cm2) | Run #3 (mcg/cm2) | Run #4 (mcg/cm2) |
|---|---|---|---|---|
| Sample Collection Point |  |  |  |  |
| API 0.5% Xylene Cyanol in Petrolatum Square root of time (hr) | Xylene Cyanol Infinite Dose, Receptor Fluid: Isopropyl alcohol:water 50:50 v:v | | | |
| 0.00 | BDL | BDL | BDL | BDL |
| 1.41 | BDL | BDL | BDL | BDL |
| 2.00 | BDL | BDL | BDL | BDL |
| 2.45 | BDL | BDL | BDL | BDL |
| 2.83 | BDL | BDL | BDL | BDL |
| 3.16 | BDL | BDL | BDL | BDL |
| Slope | Not applicable | Not applicable | Not applicable | Not applicable |
| Slope - Average | Not applicable |  |  |  |
| Slope - Standard deviation | Not applicable |  |  |  |
| Coefficient of variation | Not applicable |  |  |  |
| R Squared | Not applicable | Not applicable | Not applicable | Not applicable |

BDL: Below detection limit.

The results showed that there was no release of Xylene Cyanol into the one-phase receptor fluid. Thus, isopropyl alcohol:water in a ratio of 50 to 50 as a receptor fluid did not yield satisfactory results.

EXAMPLE 6

In Vitro Release Testing (Comparative).

The ointment containing Xylene Cyanol was used in the in vitro release testing. The receptor fluid was 1-octanol (one-phase solvent system). Total volume of the receptor fluid is 12.0 milliliter.

The following tables contain a summary of the results.

|  | Run #1 (mcg/cm2) | Run #2 (mcg/cm2) | Run #3 (mcg/cm2) | Run #4 (mcg/cm2) |
|---|---|---|---|---|
| Sample Collection Point |  |  |  |  |
| API 0.5% Xylene Cyanol in Petrolatum Square root of time (hr) | Xylene Cyanol Infinite Dose, Receptor Fluid: 1-Octanol | | | |
| 0.00 | BDL | BDL | BDL | BDL |
| 1.41 | BDL | BDL | BDL | BDL |
| 2.00 | BDL | BDL | BDL | BDL |
| 2.45 | BDL | BDL | BDL | BDL |
| 2.83 | BDL | BDL | BDL | BDL |
| 3.16 | BDL | BDL | BDL | BDL |
| Slope | Not applicable | Not applicable | Not applicable | Not applicable |
| Slope - Average | Not applicable |  |  |  |
| Slope - Standard deviation | Not applicable |  |  |  |

-continued

|  | Run #1 (mcg/cm2) | Run #2 (mcg/cm2) | Run #3 (mcg/cm2) | Run #4 (mcg/cm2) |
|---|---|---|---|---|
| Coefficient of variation | Not applicable |  |  |  |
| R Squared | Not applicable | Not applicable | Not applicable | Not applicable |

BDL: Below detection limit.

The results showed that there was no release of Xylene Cyanol into the one-phase receptor fluid. Thus, 1-octanol as a receptor fluid did not yield satisfactory results.

EXAMPLE 7

In Vitro Release Testing (Comparative).

The ointment containing Xylene Cyanol was used in the in vitro release testing. The receptor fluid was dimethyl sulfoxide:ethanol in a ratio of 50 to 50 in volume (one-phase solvent system). Total volume of the receptor fluid is 12.0 milliliter.

The following tables contain a summary of the results.

|  | Run #1 (mcg/cm2) | Run #2 (mcg/cm2) | Run #3 (mcg/cm2) | Run #4 (mcg/cm2) |
|---|---|---|---|---|
| Sample Collection Point |  |  |  |  |
| API 0.5% Xylene Cyanol in Petrolatum Square root of time (hr) | Xylene Cyanol Infinite Dose, Receptor Fluid: dimethyl sulfoxide:ethanol 50:50 v:v | | | |
| 0.00 | BDL | BDL | BDL | BDL |
| 1.41 | BDL | BDL | BDL | BDL |
| 2.00 | BDL | BDL | BDL | BDL |
| 2.45 | BDL | BDL | BDL | BDL |
| 2.83 | BDL | BDL | BDL | BDL |
| 3.16 | BDL | BDL | BDL | BDL |
| Slope | Not applicable | Not applicable | Not applicable | Not applicable |
| Slope - Average | Not applicable |  |  |  |
| Slope - Standard deviation | Not applicable |  |  |  |
| Coefficient of variation | Not applicable |  |  |  |
| R Squared | Not applicable | Not applicable | Not applicable | Not applicable |

BDL: Below detection limit.

The results showed that there was no release of Xylene Cyanol into the one-phase receptor fluid. Thus, dimethyl sulfoxide:ethanol 50:50 v:v as a receptor fluid did not yield satisfactory results.

EXAMPLE 7

In Vitro Release Testing (Comparative).

The ointment containing Xylene Cyanol was used in the in vitro release testing. The receptor fluid was 1-octanol: ethanol in a ratio of 50 to 50 in volume (one-phase solvent system). Total volume of the receptor fluid is 12.0 milliliter.

The following tables contain a summary of the results.

|  | Run #1 (mcg/cm2) | Run #2 (mcg/cm2) | Run #3 (mcg/cm2) | Run #4 (mcg/cm2) |
|---|---|---|---|---|
| Sample Collection Point |  |  |  |  |
| API 0.5% Xylene Cyanol in Petrolatum Square root of time (hr) | Xylene Cyanol Infinite Dose, Receptor Fluid: 1-octanol:ethanol 50:50 v:v | | | |
| 0.00 | BDL | BDL | BDL | BDL |
| 1.41 | BDL | BDL | BDL | BDL |
| 2.00 | BDL | BDL | BDL | BDL |
| 2.45 | BDL | BDL | BDL | BDL |
| 2.83 | BDL | BDL | BDL | BDL |
| 3.16 | BDL | BDL | BDL | BDL |
| Slope | Not applicable | Not applicable | Not applicable | Not applicable |
| Slope - Average | Not applicable |  |  |  |
| Slope - Standard deviation | Not applicable |  |  |  |
| Coefficient of variation | Not applicable |  |  |  |
| R Squared | Not applicable | Not applicable | Not applicable | Not applicable |

BDL: Below detection limit.

The results showed that there was no release of Xylene Cyanol into the one-phase receptor fluid. Thus, 1-octanol: ethanol 50:50 v:v as a receptor fluid did not yield satisfactory results.

EXAMPLE 8

In Vitro Release Testing (Comparative).

The ointment containing Xylene Cyanol was used in the in vitro release testing. The receptor fluid was dimethyl sulfoxide:isopropyl alcohol:water in a ratio of 30 to 30 to 40 in volume (one-phase solvent system). Total volume of the receptor fluid is 12.0 milliliter.

The following tables contain a summary of the results.

|  | Run #1 (mcg/cm2) | Run #2 (mcg/cm2) | Run #3 (mcg/cm2) | Run #4 (mcg/cm2) |
|---|---|---|---|---|
| Sample Collection Point |  |  |  |  |
| API 0.5% Xylene Cyanol in Petrolatum Square root of time (hr) | Xylene Cyanol Infinite Dose, Receptor Fluid: dimethyl sulfoxide:isopropyl alcohol:water 30:30:40 v:v:v | | | |
| 0.00 | BDL | BDL | BDL | BDL |
| 1.41 | BDL | BDL | BDL | BDL |
| 2.00 | BDL | BDL | BDL | BDL |
| 2.45 | BDL | BDL | BDL | BDL |
| 2.83 | BDL | BDL | BDL | BDL |
| 3.16 | BDL | BDL | BDL | BDL |
| Slope | Not applicable | Not applicable | Not applicable | Not applicable |
| Slope - Average | Not applicable |  |  |  |
| Slope - Standard deviation | Not applicable |  |  |  |

-continued

|  | Run #1 (mcg/cm2) | Run #2 (mcg/cm2) | Run #3 (mcg/cm2) | Run #4 (mcg/cm2) |
|---|---|---|---|---|
| Coefficient of variation | Not applicable | | | |
| R Squared | Not applicable | Not applicable | Not applicable | Not applicable |

BDL: Below detection limit.

The results showed that there was no release of Xylene Cyanol into the one-phase receptor fluid. Thus, dimethyl sulfoxide:isopropyl alcohol:water 30:30:40 v:v:v as a receptor fluid did not yield satisfactory results.

EXAMPLE 9

In Vitro Release Testing (Present Disclosure).

The ointment containing Xylene Cyanol was used in the in vitro release testing. 1-Octanol was selected as the water-immiscible phase. Water was selected as the aqueous phase. The ratio of 1-octanol to water is 50 to 50 in volume. Total volume of the receptor fluid is 12.0 milliliter.

The following tables contain a summary of the results.

|  | Run #1 (mcg/cm2) | Run #2 (mcg/cm2) | Run #3 (mcg/cm2) | Run #4 (mcg/cm2) |
|---|---|---|---|---|
| Sample Collection Point | | | | |
| API 0.5% Xylene Cyanol in Petrolatum Square root of time (hr) | Xylene Cyanol Infinite Dose, Receptor Fluid: 1-Octanol:H$_2$O 1:1 v:v | | | |
| 0.00 | 0.0000 | 0.0000 | 0.0000 | 0.0000 |
| 1.41 | 0.4956 | 1.0261 | 0.4914 | 0.4640 |
| 2.00 | 1.2143 | 1.9575 | 1.4206 | 1.4438 |
| 2.45 | 2.2025 | 3.0973 | 2.5204 | 2.5436 |
| 2.83 | 3.1044 | 4.1192 | 3.3865 | 3.7213 |
| 3.16 | 3.8674 | 4.8589 | 4.2884 | 4.5853 |
| Slope | 1.9686 | 2.2516 | 2.1875 | 2.4026 |
| Slope - Average | 2.2026 | | | |
| Slope - Standard deviation | 0.1802 | | | |
| Coefficient of variation | 8.18% | | | |
| R Squared | 0.9826 | 0.9902 | 0.9905 | 0.9862 |

As shown in FIG. 1, a plot of amount of xylene cyanol released into the receptor fluid in unit of microgram per square centimeter of the membrane as a function of square root of time of the sampling hours yields release rate of xylene cyanol from the ointment. R Squared value is a statistical measure of how close the released data are to the fitted regression line. An R Squared value of 1.000 indicates a linear release. An R squared value of 0.9000 or greater is generally considered as satisfactory in terms of release linearity.

All of the runs show satisfactory R Squared values with narrow overall coefficient of variation.

EXAMPLE 10

In Vitro Release Testing (Present Disclosure).

The ointment containing Xylene Cyanol was used in the in vitro release testing. 1-Octanol was selected as the water-immiscible phase. A phosphate buffer solution (PBS), pH 7.4, (composition: 10 millimolar phosphate, 138 millimolar sodium chloride, and 2.7 millimolar potassium chloride in water) was selected as the aqueous phase. The ratio of 1-octanol to the PBS buffer is 50 to 50 in volume. Total volume of the receptor fluid is 12.0 milliliter.

TABLE 2

The following tables contain a summary of the results.

|  | Run #1 (mcg/cm2) | Run #2 (mcg/cm2) | Run #3 (mcg/cm2) | Run #4 (mcg/cm2) |
|---|---|---|---|---|
| Sample Collection Point | | | | |
| API 0.5% Xylene Cyanol in Petrolatum Square root of time | Xylene Cyanol Infinite Dose, Receptor Fluid: 1-Octanol:PBS Buffer pH 7.4 1:1 v:v | | | |
| 0.00 | 0.0000 | 0.0000 | 0.0000 | 0.0000 |
| 1.41 | 0.0000 | 0.0000 | 0.0000 | 0.2926 |
| 2.00 | 0.3389 | 0.4105 | 0.5179 | 0.4295 |
| 2.45 | 1.2295 | 1.3179 | 0.8863 | 0.9032 |
| 2.83 | 1.3579 | 1.8147 | 1.4400 | 1.5937 |
| 3.16 | 1.8884 | 2.4316 | 1.7305 | 1.9768 |
| Slope | 1.1014 | 1.4283 | 1.0060 | 1.0163 |
| Slope - Average | 1.0412 | | | |
| Slope - Standard deviation | 0.0524 | | | |
| Coefficient of variation | 5.03% | | | |
| R Squared | 0.9576 | 0.9731 | 0.9902 | 0.9168 |

The following tables contain a summary of the results.

Figure 2:
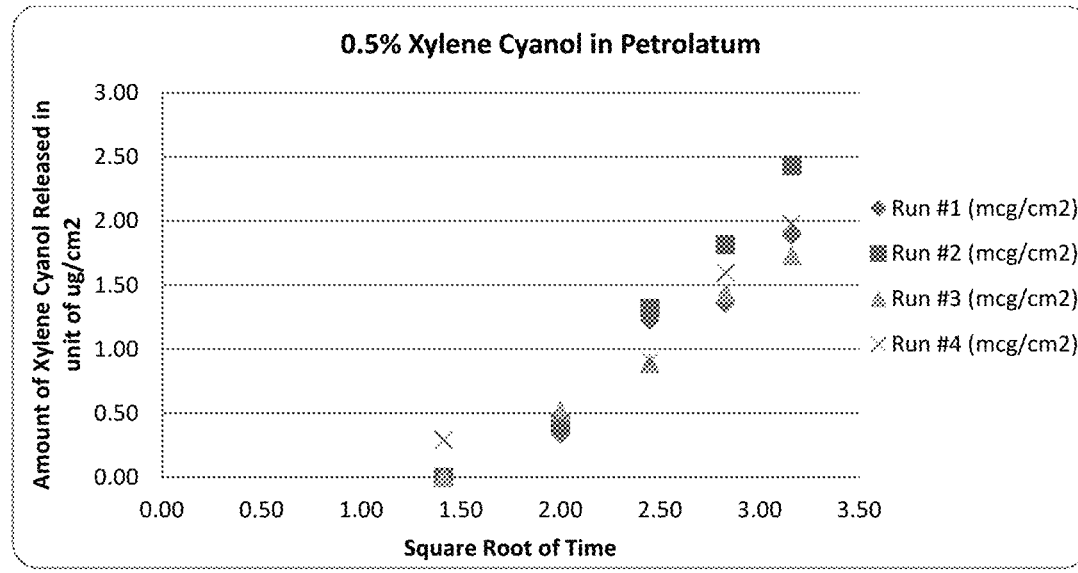
FIG. 2 illustrates an amount of xylene cyanol released in microgram per square centimeters of the membrane as a function of square root of release time in hours according to another embodiment.

As shown in FIG. 2, a plot of amount of xylene cyanol released into the receptor fluid in unit of microgram per square centimeter of the membrane as a function of square root of time of the sampling hours yields release rate of xylene cyanol from the ointment. R Squared value is a statistical measure of how close the released data are to the fitted regression line. An R Squared value of 1.000 indicates a linear release. An R squared value of 0.9000 or greater is generally considered as satisfactory in terms of release linearity.

All of the runs show satisfactory R Squared values with narrow overall coefficient of variation.

EXAMPLE 11

In Vitro Release Testing (Present Disclosure).

A biphasic receptor fluid of the present disclosure might be suitable to test release of xylene cyanol from the ointment containing xylene cyanol.

A biphasic receptor fluid consisting of 1-octanol:ethanol:water 40:20:40 v:v:v might be suitable in an IVRT experiment to test release of xylene cyanol from the ointment. Ethanol is expected to be distributed in both 1-octanol and water phase. Presence of ethanol in the water phase is expected to increase solubility of xylene cyanol in the water phase. It is believed that higher amount of xylene cyanol would be released into the water phase.

EXAMPLE 12

In Vitro Release Testing (Present Disclosure).

A biphasic receptor fluid of the present disclosure might be suitable to test release of xylene cyanol from the ointment containing xylene cyanol.

A biphasic receptor fluid consisting of 1-octanol:isopropanol:water 40:20:40 v:v:v might be suitable in an IVRT experiment to test release of xylene cyanol from the ointment. Isopropanol is expected to be distributed in both 1-octanol and water phase. Presence of isopropanol in the water phase is expected to increase solubility of xylene cyanol in the water phase. It is believed that higher amount of xylene cyanol would be released into the water phase.

EXAMPLE 13

In Vitro Release Testing (Present Disclosure).

A biphasic receptor fluid of the present disclosure might be suitable to test release of xylene cyanol from the ointment containing xylene cyanol.

A biphasic receptor fluid consisting of 1-octanol:glycerin:water 40:20:40 v:v:v might be suitable in an IVRT experiment to test release of xylene cyanol from the ointment. Glycerin is expected to be distributed in both 1-octanol and water phase. Presence of glycerin in the water phase is expected to increase solubility of xylene cyanol in the water phase. It is believed that higher amount of xylene cyanol would be released into the water phase.

EXAMPLE 14

In Vitro Release Testing (Present Disclosure).

A biphasic receptor fluid of the present disclosure might be suitable to test release of xylene cyanol from the ointment containing xylene cyanol.

A biphasic receptor fluid consisting of 1-octanol:PEG 400:water 40:20:40 v:v:v might be suitable in an IVRT experiment to test release of xylene cyanol from the ointment. PEG 400 is expected to be distributed in both 1-octanol and water phase. Presence of PEG 400 in the water phase is expected to increase solubility of xylene cyanol in the water phase. It is believed that higher amount of xylene cyanol would be released into the water phase.

EXAMPLE 15

In Vitro Release Testing (Present Disclosure).

A biphasic receptor fluid of the present disclosure might be suitable to test release of xylene cyanol from the ointment containing xylene cyanol.

A biphasic receptor fluid consisting of 1-octanol:propylene glycol:water 40:20:40 v:v:v might be suitable in an IVRT experiment to test release of xylene cyanol from the ointment. Propylene glycol is expected to be distributed in both 1-octanol and water phase. Presence of propylene glycol in the water phase is expected to increase solubility of xylene cyanol in the water phase. It is believed that higher amount of xylene cyanol would be released into the water phase.

EXAMPLE 16

In Vitro Release Testing (Present Disclosure).

A biphasic receptor fluid of the present disclosure might be suitable to test release of xylene cyanol from the ointment containing xylene cyanol.

A biphasic receptor fluid consisting of 1-hexanol:water 50:50 v:v might be suitable in an IVRT experiment to test release of xylene cyanol from the ointment. 1-Hexanol has higher solubility in water than 1-octanol. It is expected that higher amount of 1-hexanol would be distributed in the water phase, thereby enhancing solubility of xylene cyanol in the water phase. It is believed that high amount of xylene cyanol would be released into the water phase.

EXAMPLE 17

In Vitro Release Testing (Present Disclosure).

A biphasic receptor fluid of the present disclosure might be suitable to test release of xylene cyanol from the ointment containing xylene cyanol.

A biphasic receptor fluid consisting of 1-hexanol:1-octanol:water 25:25:50 v:v:v might be suitable in an IVRT experiment to test release of xylene cyanol from the ointment. 1-Hexanol has higher solubility in water than 1-octanol. It is expected that higher amount of 1-hexanol would be distributed in the water phase, thereby enhancing solubility of xylene cyanol in the water phase. It is believed that high amount of xylene cyanol would be released into the water phase.

EXAMPLE 18

In Vitro Release Testing (Present Disclosure).

A biphasic receptor fluid of the present disclosure might be suitable to test release of xylene cyanol from the ointment containing xylene cyanol.

A biphasic receptor fluid consisting of 1-butanol:1-octanol:water 20:30:50 v:v:v might be suitable in an IVRT experiment to test release of xylene cyanol from the ointment. 1-Butanol has higher solubility in water than 1-octanol. It is expected that higher amount of 1-butanol would be distributed in the water phase, thereby enhancing solubility of xylene cyanol in the water phase. It is believed that high amount of xylene cyanol would be released into the water phase.

EXAMPLE 19

In Vitro Release Testing (Present Disclosure).

A biphasic receptor fluid of the present disclosure might be suitable to test release of two pharmaceutically active compounds from an ointment.

Ointment Dosage Form

| Ingredients | Percentage (%) |
|---|---|
| Loteprednol etabonate | 0.5 |
| Tobramycin sulfate | 0.3 |
| Petrolatum | 99.2 |

Loteprednol etabonate is a lipophilic corticosteroid. Tobramycin sulfate is an antibiotic, which is freely soluble in water. They possess very different lipophilicity and hydrophilicity. A biphasic receptor fluid consisting of 1-octanol:1-hexanol:water 25:25:50 v:v:v might be suitable in an IVRT experiment to test release of loteprednol etabonate and tobramycin sulfate from the ointment. It is expected that the released loteprednol etabonate would be mostly solubilized in the organic 1-octanol/1-hexanol phase and tobramycin sulfate would be mostly solubilized in the water phase.

It will be apparent to those skilled in the art that the methods and apparatuses disclosed herein could be applied to a variety of structures having different geometries and to create selectively coated and uncoated portions of varying shapes, sizes, and orientations. It will also be apparent to those skilled in the art that various modifications and variations can be made without departing from the spirit or scope of the disclosure.

What is claimed is:

1. A system for testing a bioactive agent comprising:
   a barrier membrane;
   a donor formulation; and
   a biphasic receptor system comprising fluids of different phases that are immiscible.

2. The system of claim 1, wherein the biphasic receptor system comprises at least one hydrophilic phase and at least one hydrophobic phase.

3. The system of claim 2, wherein the at least one hydrophobic phase is an alcohol with five or more carbons, an ester, an alkane, alkene, or a combinations thereof.

4. The system of claim 2, wherein the at least one hydrophobic phase is an alcohol selected from a group consisting of 1-pentanol, 1-hexanol, 1-heptanol, 1-octanol, 1-nonanol, 1-decanol, 1-undecanol, cyclopentanol, cyclohexanol, 3-pentanol, 2-hexanol, 3-hexanol, 2-heptanol, 2-octanol, 1,2-heptanediol, 1,2-octanediol, and combinations thereof.

5. The system of claim 2, wherein the at least one hydrophobic phase is an ester selected from a group consisting of ethyl acetate, caprylic/capric triglyceride, isopropyl myristate, isopropyl palmitate, diisopropyl adipate, castor oil, olive oil, coconut oil, cochin oil, corn oil, cottonseed oil, linseed oil, palm oil, palm kernel oil, peanut oil, soybean oil, sunflower oil, tall oils, tallow, tung oil, whale oil, tea seed oil, sesame seed oil, safflower oil, rapeseed oil, fish oils, and a combination thereof.

6. The system of claim 2, wherein the at least one hydrophobic phase is an alkane selected from a group consisting of isododecane, squalane, and a combination thereof.

7. The system of claim 2, wherein the hydrophilic phase is suitable aqueous-based solvent comprising water or water solution.

8. The system of claim 7, wherein water solution further comprises a salt, a pH-adjusting agent, an anti-oxidant, a buffering agent, a preservative, or a combination thereof.

9. The system of claim 7, wherein the water solution further contains water-miscible organic solvents.

10. The system of claim 9, wherein the water-miscible organic solvents are selected from a group consisting of monohydric alcohols, polyhydric alcohols, polyalkenyl alcohols, N-alkyl-2-pyrrolidones, isosorbide type of solvents, dimethyl sulfoxide, dimethylformide, dimethyl acetamide, and combinations thereof.

11. The system of claim 9, wherein the water-miscible organic solvents are monohydric alcohols selected from a group consisting of ethanol, 1-propanol, isopropanol, and 1-butanol.

12. The system of claim 9, wherein the water-miscible organic solvents are polyhydric alcohols selected from a group consisting of glycerin, propylene glycol, butylene glycol, and hexylene glycol.

13. The system of claim 9, wherein the water-miscible organic solvents are N-alkyl-2-pyrrolidones selected from a group consisting of N-methyl-2-pyrrolidone, N-ethyl-2-pyrrolidone, and N-propyl-2-pyrrolidone.

14. The system of claim 2, wherein the donor formulation is an ointment.

15. An in vitro release testing method for testing the ability of formulations to deliver bioactive agents across a barrier membrane, comprising the steps of:
   (i) providing a dosage of a semi-solid formulation containing the bioactive agent, a receptor and a barrier membrane to separate the semi-solid formulation and the receptor fluid;
   (ii) contacting the semi-solid formulation with one side of the barrier membrane and the receptor fluid with the other side of the barrier membrane for a time sufficient to produce penetration of the barrier membrane by the semi-solid formulation; and,
   (iii) sampling the receptor fluid and assaying the same to determine the concentration of the bioactive agent in the receptor fluid, wherein the receptor fluid is a biphasic system comprising fluids of different phases that are immiscible.

16. The in vitro release testing method of claim 15, wherein the biphasic system comprises at least one hydrophilic phase and at least one hydrophobic phase.

17. The in vitro release testing method of claim 16, wherein the at least one hydrophobic phase is an alcohol with five or more carbons, an ester, an alkene and an alkane.

18. The in vitro release testing method of claim 17, wherein the alcohol is selected from a group consisting of 1-pentanol, 1-hexanol, 1-heptanol, 1-octanol, 1-nonanol, 1-decanol, 1-undecanol, cyclopentanol, cyclohexanol, 3-pentanol, 2-hexanol, 3-hexanol, 2-heptanol, 2-octanol, 1,2-heptanediol, 1,2-octanediol, and combinations thereof.

19. The in vitro release testing of claim 17, wherein the ester is selected from a group consisting of ethyl acetate, caprylic/capric triglyceride, isopropyl myristate, isopropyl palmitate, diisopropyl adipate, castor oil, olive oil, coconut oil, cochin oil, corn oil, cottonseed oil, linseed oil, palm oil, palm kernel oil, peanut oil, soybean oil, sunflower oil, tall oils, tallow, tung oil, whale oil, tea seed oil, sesame seed oil, safflower oil, rapeseed oil, fish oils, and a combination thereof.

20. The in vitro release testing of claim 17, wherein the alkane is selected from a group consisting of isododecane, squalane, and a combination thereof.

21. The in vitro release testing of claim 16, wherein the hydrophilic phase is suitable aqueous-based solvent comprising water or water solution.

22. The in vitro release testing of claim 21, wherein the water solution further comprises a salt, a pH-adjusting agent, an anti-oxidant, a buffering agent, a preservative, or a combination thereof.

23. The in vitro release testing of claim 21, wherein the water solution further contains water-miscible organic solvents.

24. The in vitro release testing of claim 23, wherein the water-miscible organic solvents are selected from a group consisting of monohydric alcohols, polyhydric alcohols, polyalkenyl alcohols, N-alkyl-2-pyrrolidones, isosorbide type of solvents, dimethyl sulfoxide, dimethylformide, dimethyl acetamide, and combinations thereof.

25. The in vitro release testing of claim 24, wherein the water-miscible organic solvents are N-alkyl-2-pyrrolidones selected from a group consisting of N-methyl-2-pyrrolidone, N-ethyl-2-pyrrolidone, and N-propyl-2-pyrrolidone.

26. The in vitro release testing of claim 23, wherein the water-miscible organic solvents are monohydric alcohols selected from a group consisting of monohydric alcohols are ethanol, isopropanol, and 1-butanol.

27. The in vitro release testing of claim 23, wherein the water-miscible organic solvents are polyhydric alcohols selected from a group consisting of glycerin, propylene glycol, butylene glycol, and hexylene glycol.

28. The system of claim 15, wherein the semi-solid formulation has a petrolatum base.

29. A system for testing a bioactive agent comprising a donor formulation and a receptor, the receptor comprises:
a biphasic system, wherein the biphasic system comprises one hydrophilic phase and at least one hydrophobic phase; and
wherein the at least one hydrophobic phase is an alcohol with five or more carbons, an ester, an alkene and an alkane.

30. The system of claim 29, wherein the alcohol is selected from a group consisting of 1-pentanol, 1-hexanol, 1-heptanol, 1-octanol, 1-nonanol, 1-decanol, 1-undecanol, cyclopentanol, cyclohexanol, 3-pentanol, 2-hexanol, 3-hexanol, 2-heptanol, 2-octanol, 1,2-heptanediol, 1,2-octanediol, and combinations thereof.

31. The system of claim 29, wherein the ester is selected from a group consisting of ethyl acetate, caprylic/capric triglyceride, isopropyl myristate, isopropyl palmitate, diisopropyl adipate, castor oil, olive oil, coconut oil, cochin oil, corn oil, cottonseed oil, linseed oil, palm oil, palm kernel oil, peanut oil, soybean oil, sunflower oil, tall oils, tallow, tung oil, whale oil, tea seed oil, sesame seed oil, safflower oil, rapeseed oil, fish oils, and a combination thereof.

32. The system of claim 29, wherein the alkane is selected from a group consisting of isododecane, squalane, and a combination thereof.

33. The system of claim 29, wherein a volume ratio of the hydrophilic phase and the at least one hydrophobic phase is within a range of 99 to 1 to 1 to 99.

34. A system for testing a bioactive agent comprising a donor formulation and a receptor, the receptor comprises: a biphasic system, wherein the biphasic system comprises one hydrophilic phase and at least one hydrophobic phase, wherein the hydrophilic phase is a suitable aqueous-based solvent comprising water or water solution, and wherein the water solution further contains water-miscible organic solvents.

35. The system of claim 34, wherein the water solution further comprises a salt, a pH-adjusting agent, an antioxidant, a buffering agent, a preservative, or a combination thereof.

36. The system of claim 34, wherein the water-miscible organic solvents are selected from a group consisting of monohydric alcohols, polyhydric alcohols, polyalkenyl alcohols, N-alkyl-2-pyrrolidones, isosorbide type of solvents, dimethyl sulfoxide, dimethylformide, dimethyl acetamide, and a combination thereof.

37. The system of claim 34, wherein the water-miscible organic solvents are monohydric alcohols selected from a group consisting ethanol, isopropanol, and 1-butanol.

38. The system of claim 34, wherein the water-miscible organic solvents are polyhydric alcohols selected from a group consisting of glycerin, propylene glycol, butylene glycol, and hexylene glycol.

39. The system of claim 34, wherein the water-miscible organic solvents are N-alkyl-2-pyrrolidones selected from a group consisting of N-methyl-2-pyrrolidone, N-ethyl-2-pyrrolidone, and N-propyl-2-pyrrolidone.

* * * * *